US 6,942,627 B2
Sep. 13, 2005

(12) United States Patent
Huitema

(10) Patent No.: US 6,942,627 B2
(45) Date of Patent: Sep. 13, 2005

(54) SURGICAL BIOPSY DEVICE HAVING A FLEXIBLE CUTTER

(75) Inventor: Thomas W. Huitema, Fremont, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/908,893

(22) Filed: Jul. 19, 2001

(65) Prior Publication Data

US 2003/0018281 A1 Jan. 23, 2003

(51) Int. Cl.⁷ .............................................. A61B 10/00
(52) U.S. Cl. ...................... 600/566; 600/568; 600/567; 606/167
(58) Field of Search ................................. 600/562, 564, 600/565, 566, 567, 568, 464; 606/167, 197

(56) References Cited

U.S. PATENT DOCUMENTS

| 4,250,892 | A |   | 2/1981  | Dolhay et al. |         |
|-----------|---|---|---------|-----------------|---------|
| 4,320,761 | A |   | 3/1982  | Haddad          |         |
| 4,535,773 | A |   | 8/1985  | Yoon            |         |
| 4,823,685 | A |   | 4/1989  | Boumans et al.  |         |
| 4,935,005 | A |   | 6/1990  | Haines          |         |
| 5,027,827 | A |   | 7/1991  | Cody et al.     |         |
| 5,197,484 | A |   | 3/1993  | Kornberg et al. |         |
| 5,213,110 | A |   | 5/1993  | Kedem et al.    |         |
| 5,219,351 | A | * | 6/1993  | Teubner et al.  | 606/130 |
| 5,224,470 | A |   | 7/1993  | Schneep-Pesch et al. |    |
| 5,236,334 | A |   | 8/1993  | Bennett         |         |
| 5,243,994 | A |   | 9/1993  | Ranalletta      |         |
| 5,249,582 | A |   | 10/1993 | Taylor          |         |
| 5,249,583 | A |   | 10/1993 | Mallaby         |         |
| 5,275,609 | A |   | 1/1994  | Pingleton et al.|         |
| 5,282,476 | A |   | 2/1994  | Terwilliger     |         |
| 5,284,156 | A |   | 2/1994  | Schramm et al.  |         |
| 5,318,528 | A | * | 6/1994  | Heaven et al.   | 600/564 |
| 5,333,619 | A |   | 8/1994  | Burgio          |         |
| 5,341,816 | A |   | 8/1994  | Allen           |         |
| 5,353,804 | A |   | 10/1994 | Kornberg et al. |         |
| 5,368,045 | A |   | 11/1994 | Clement et al.  |         |
| 5,394,887 | A |   | 3/1995  | Haaga           |         |
| 5,398,690 | A | * | 3/1995  | Batten et al.   | 600/439 |
| 5,400,798 | A |   | 3/1995  | Baran           |         |
| 5,403,276 | A |   | 4/1995  | Schechter et al.|         |
| 5,409,013 | A |   | 4/1995  | Clement         |         |
| 5,415,182 | A |   | 5/1995  | Chin et al.     |         |
| 5,458,112 | A |   | 10/1995 | Weaver          |         |
| 5,487,392 | A |   | 1/1996  | Haaga           |         |
| 5,492,130 | A |   | 2/1996  | Chiou           |         |
| 5,505,210 | A |   | 4/1996  | Clement         |         |
| 5,507,298 | A |   | 4/1996  | Schramm et al.  |         |

(Continued)

FOREIGN PATENT DOCUMENTS

| WO | 95/27443 A1 | 10/1995 |
|----|-------------|---------|
| WO | 97/47243 A1 | 12/1997 |
| WO | 98/09561 A2 | 3/1998  |

OTHER PUBLICATIONS

Merriam–Webster's Collegiate Dictionary. Merriam–Webster, Inc. 10ᵗʰ ed. 2001.*

Primary Examiner—Max F. Hindenburg
Assistant Examiner—Jonathan Foreman

(57) ABSTRACT

A biopsy probe for the collection of at least one soft tissue sample from a surgical patient. The biopsy probe has a frame and an elongated piercing element having a proximal end attached to the distal end of the frame and a sharpened distal end for piercing tissue. The piercing element has a lumen extending at least partially therethrough. The probe also includes an elongated cutter disposed coaxially and slidably within the lumen of the piercing element. The cutter has a distal end for cutting a tissue sample, a proximal end and a body connecting the distal and proximal ends, wherein at least a portion of the body comprises a flexible member.

10 Claims, 5 Drawing Sheets

U.S. PATENT DOCUMENTS

| | | | |
|---|---|---|---|
| 5,511,556 A | | 4/1996 | DeSantis |
| 5,526,821 A | | 6/1996 | Jamshidi |
| 5,526,822 A | | 6/1996 | Burbank et al. |
| 5,535,755 A | | 7/1996 | Heske |
| 5,538,008 A | * | 7/1996 | Crowe .................. 600/564 |
| 5,560,373 A | | 10/1996 | De Santis |
| 5,562,102 A | | 10/1996 | Taylor |
| 5,564,436 A | | 10/1996 | Hakky et al. |
| 5,573,008 A | | 11/1996 | Robinson et al. |
| 5,595,185 A | | 1/1997 | Erlich |
| 5,601,585 A | * | 2/1997 | Banik et al. .............. 606/180 |
| 5,603,724 A | | 2/1997 | O'Connor |
| 5,607,389 A | | 3/1997 | Edwards et al. |
| 5,615,690 A | | 4/1997 | Giurtino et al. |
| 5,643,304 A | | 7/1997 | Schechter et al. |
| 5,649,547 A | | 7/1997 | Richart et al. |
| 5,669,876 A | | 9/1997 | Schechter et al. |
| 5,685,838 A | | 11/1997 | Peters et al. |
| 5,685,840 A | | 11/1997 | Schechter et al. |
| 5,697,898 A | | 12/1997 | Devine |
| 5,755,731 A | * | 5/1998 | Grinberg .................. 606/170 |
| 5,769,086 A | | 6/1998 | Richart et al. |
| 5,775,333 A | | 7/1998 | Burbank et al. |
| 5,827,305 A | * | 10/1998 | Gordon .................. 606/159 |
| 5,924,977 A | * | 7/1999 | Yabe et al. .............. 600/121 |
| 5,928,164 A | | 7/1999 | Burbank et al. |
| 6,007,497 A | | 12/1999 | Huitema |
| 6,019,733 A | | 2/2000 | Faraschioni |
| 6,022,362 A | * | 2/2000 | Lee et al. .................. 600/564 |
| 6,027,514 A | * | 2/2000 | Stine et al. .............. 600/564 |
| 6,053,907 A | | 4/2000 | Zirps |
| 6,149,607 A | * | 11/2000 | Simpson et al. .......... 600/564 |
| 6,261,242 B1 | * | 7/2001 | Roberts et al. .......... 600/564 |
| 6,325,796 B1 | * | 12/2001 | Berube et al. .............. 606/33 |
| 6,419,641 B1 | * | 7/2002 | Mark et al. .............. 600/564 |
| 6,514,215 B1 | * | 2/2003 | Ouchi .................. 600/564 |
| 2002/0120211 A1 | * | 8/2002 | Wardle et al. .......... 600/564 |

* cited by examiner

SURGICAL BIOPSY DEVICE HAVING A FLEXIBLE CUTTER

FIELD OF THE INVENTION

The present invention relates, in general, to devices for tissue sampling and, more particularly, to improved biopsy probes for acquiring subcutaneous biopsies and for removing lesions.

BACKGROUND OF THE INVENTION

The diagnosis and treatment of patients with cancerous tumors, pre-malignant conditions, and other disorders has long been an area of intense investigation. Non-invasive methods for examining tissue are palpation, X-ray, MRI, CT, and ultrasound imaging. When the physician suspects that a tissue may contain cancerous cells, a biopsy may be done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. For a percutaneous biopsy, a needle-like instrument is used through a very small incision to access the tissue mass of interest and to obtain a tissue sample for later examination and analysis. The advantages of the percutaneous method as compared to the open method are significant: less recovery time for the patient, less pain, less surgical time, lower cost, less risk of injury to adjacent bodily tissues such as nerves, and less disfigurement of the patient's anatomy. Use of the percutaneous method in combination with artificial imaging devices such as X-ray and ultrasound has resulted in highly reliable diagnoses and treatments.

Generally there are two ways to obtain percutaneously a portion of tissue from with the body, by aspiration or by core sampling. Aspiration of the tissue through a fine needle requires the tissue to be fragmented into small enough pieces to be withdrawn in a fluid medium. The method is less intrusive than other known sampling techniques, but one can only examine cells in the liquid (cytology) and not the cells and the structure (pathology). In core biopsy, a core or fragment of tissue is obtained for histologic examination which may be done via a frozen or paraffin section. The type of biopsy used depends mainly on various factors present in the patient, and no single procedure is ideal for all cases. Core biopsy, however, is very useful in a number of conditions and is widely used by physicians.

A number of biopsy devices for use in combination with artificial imaging devices are known in the field. An example of a core biopsy device using an artificial imaging system is described in U.S. Pat. Nos. 4,699,154, 4,944,308, and Re. 34,056. However, these types of spring-powered devices must re-puncture the breast or organ each time a sample is taken. An example of an aspiration device using an artificial imaging system is described in the following U.S. Pat. Nos.: 5,492,130 issued to Chiou on Feb. 20, 1996; 5,526,821 issued to Jamshidi on Jun. 18, 1996; 5,429,138 issue to Jamshidi on Jul. 4, 1995; and 5,027,827 issued to Cody, et al, on Jul. 2, 1991.

Operator error can often be an issue with the above described devices. In addition there was a need for a device which could enable multiple sampling of the tissue without having to re-puncture the tissue for each sample. An example of such a product is described in U.S. Pat. No. 5,526,822 issued to Burbank, et al, on Jun. 18, 1996, which is hereby incorporated herein by reference. The Burbank et al. instrument is a type of image-guided, percutaneous, coring, breast biopsy instrument. It is vacuum-assisted, and some of the steps for retrieving the tissue samples have been automated. The physician uses this device to capture "actively" (using the vacuum) the tissue prior to severing it from the body. This allows for sampling tissues of varying hardness. The device can also be used to collect multiple samples in numerous positions about its longitudinal axis, and without needing to remove the device from the body. These features allow for substantial sampling of large lesions and complete removal of small ones. In the medical arts the instrument is commonly known as MAMMO-TOME™.

Numerous improvements to the Burbank et al. device have been described in co-pending and commonly assigned U.S. application Ser. No. 08/825,899, filed on Apr. 2, 1997, the disclosure of which is hereby incorporated herein by reference. This reference describes numerous improvements to the original invention including a molded tissue cassette housing which permits the handling and viewing of multiple tissue samples without physical contact by the instrument operator. Another improvement to the original device includes the interconnection of the housing to the piercing needle by a thumbwheel which permits the needle to rotate relative to the housing, thereby preventing the vacuum tube from wrapping about the housing.

Other improvements to the above described device are disclosed in U.S. Pat. No. 6,007,497 issued to Huitema on Dec. 28, 1999, which is hereby incorporated herein by reference. This reference described improvements to the fluid management capabilities of the system, resulting in part from the addition of sealing elements located in critical areas of the biopsy probe.

In actual clinical use for breast biopsy, the MAMMO-TOME instrument (probe and driver assembly) is mounted to the three axis positioning head of an x-ray imaging machine. The three axis positioning head is located in the area between the x-ray source and the image plate. The x-ray machines are outfitted with a computerized system which requires two x-ray images of the breast be taken with the x-ray source at two different positions in order for the computer to calculate the x, y and z axis location of the suspect abnormality. In order to take the stereo x-ray images the x-ray source must be conveniently movable. The x-ray source therefore is typically mounted to an arm which, at the end opposite the x-ray source, is pivotally mounted to the frame of the machine in the region of the image plate.

To image the breast, the breast is placed between the x-ray source and the image plate, the breast being placed on the image plate. In order to take the necessary stereo images the clinician will manually position the x-ray source to one side and then the other of the center axis of the machine (typically 15–20 degrees to each side of the center axis), obtaining an x-ray image on each side of the breast. The computer will then, with great accuracy, calculate the precise x, y and z location of the suspect abnormality in the breast and automatically communicate to the clinician or directly to the positioning head the targeting coordinates for the biopsy device. The clinician can then manually, or automatically, position the biopsy probe into the breast at the precise location of the abnormality.

There are generally two styles of x-ray machines in wide spread use for breast imaging. One style is known as "prone", because the patient lies face down during the x-ray and biopsy procedures on a table that is configured horizontal to the floor. The other style, in more wide spread use, is the "upright". The center axis of the upright imaging machine is configured vertical to the floor and the patient sits in front of the machine during the x-ray and biopsy procedures.

The above described biopsy instruments mount to a three axis positioning head located between the x-ray source and image plate on the breast x-ray imaging machine. The distance between the x-ray source and imaging plate is known in the industry as the SID (Source to Image Distance). There is no standard SID in the industry and in fact the SID varies greatly from one x-ray machine manufacturer to another.

This creates a problem for the manufacturers of devices, like the MAMMOTOME, which is intended to be mounted between the x-ray source and image plate of the x-ray imaging machine. In the case of the MAMMOTOME instrument with its length from the distal tip of the biopsy probe to the most proximal portion of the driver measuring approximately 41 centimeters, adequate mounting space has been found to exist on the prone style x-ray machines. However, on some of the more popular upright style x-ray imaging machines the SID has been found to be as little as 29 centimeters, obviously too small in which to mount the MAMMOTOME. What is needed, therefore, is a biopsy instrument configured to permit mounting on the shorter SID x-ray imaging machines.

SUMMARY OF THE INVENTION

In accordance with the present invention, there is provided a biopsy probe for the collection of at least one soft tissue sample from a surgical patient. The biopsy probe has a frame and an elongated piercing element having a proximal end attached to the distal end of the frame and a sharpened distal end for piercing tissue. The piercing element has a lumen extending at least partially therethrough. The probe also includes an elongated cutter disposed coaxially and slidably within the lumen of the piercing element. The cutter has a distal end for cutting a tissue sample, a proximal end and a body connecting the distal and proximal ends, wherein at least a portion of the body comprises a flexible member.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
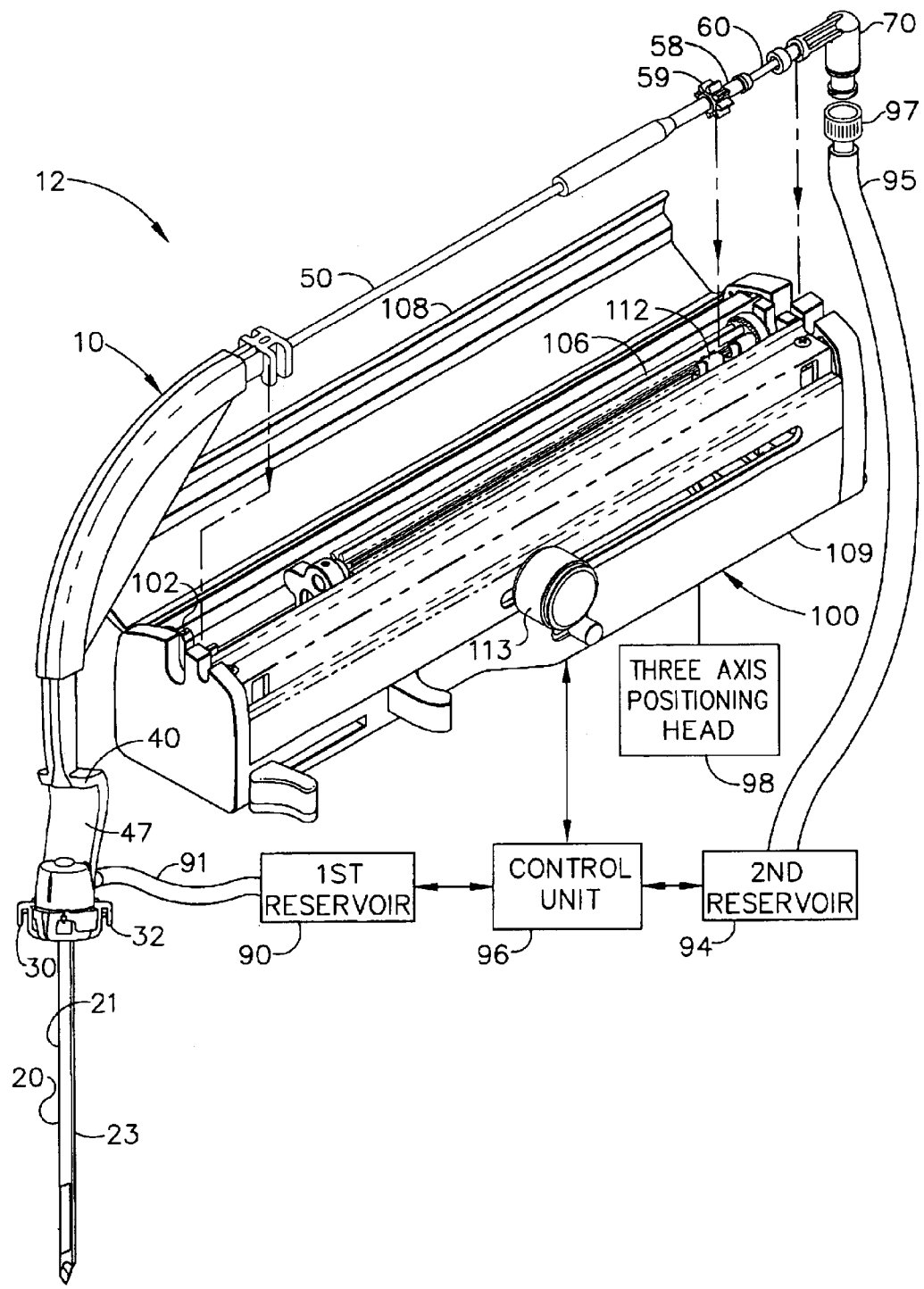
FIG. 1 is an isometric view of a biopsy apparatus, showing the biopsy probe of FIG. 2, its insertion into a driver, and schematic representations of a control unit, vacuum sources, and three axis positioning head.

As best shown in FIG. 1, the present invention is a surgical biopsy apparatus 12 for a minimally invasively acquiring repeated subcutaneous biopsies. In the present invention, surgical biopsy apparatus 12 generally comprises a probe 10 for insertion within a surgical patient for extraction of a tissue sample therefrom. Apparatus 12 further includes a powered probe driver 100, a three axis positioning head 98, a control unit 96, and a first and second tube in fluid communication with a first, and second reservoir, respectively. In the preferred embodiment, reservoirs 90 and 94 are connected to at least one vacuum source. Probe 10 of surgical biopsy apparatus 12 is removably mounted to powered probe driver 100. The elements shown schematically as boxes in FIG. 1 are well known in the art and are described in the herein incorporated references.

Driver 100 is well known in the art and includes a housing 109 having a moveable cover 108 hingedly attached thereto. Within housing 109 there is a housing mount fork 102 for receiving probe 10. Housing 109 also includes a cutter advance fork 112 for positioning cutter gear 59, and an elongated driver gear 106 to mate with and rotate cutter 50. Driver 100 is attached to a three axis positioning head 98 which is connected to an x-ray imaging machine having a stereotactic guidance system (not shown). This positioning/guidance system is for moving probe 10 and driver 100 so that the apparatus pierces the tissue at the correct location in order to sample the target lesion. Housing 109 also has a cutter advance knob 113 which is manually actuated to obtain the tissue sample. This feature will be discussed in greater detail below.

Control unit 96 is used to control the sequence of actions performed by surgical biopsy apparatus 12 in order to obtain the biopsy sample from a surgical patient. As will be appreciated by those skilled in the art, and as discussed in the hereinbefore incorporated references, control unit 96 preferably controls the application of a vacuum to probe 10, and controls the activation of the cutter motor (not shown) within driver 100.

Figure 2:
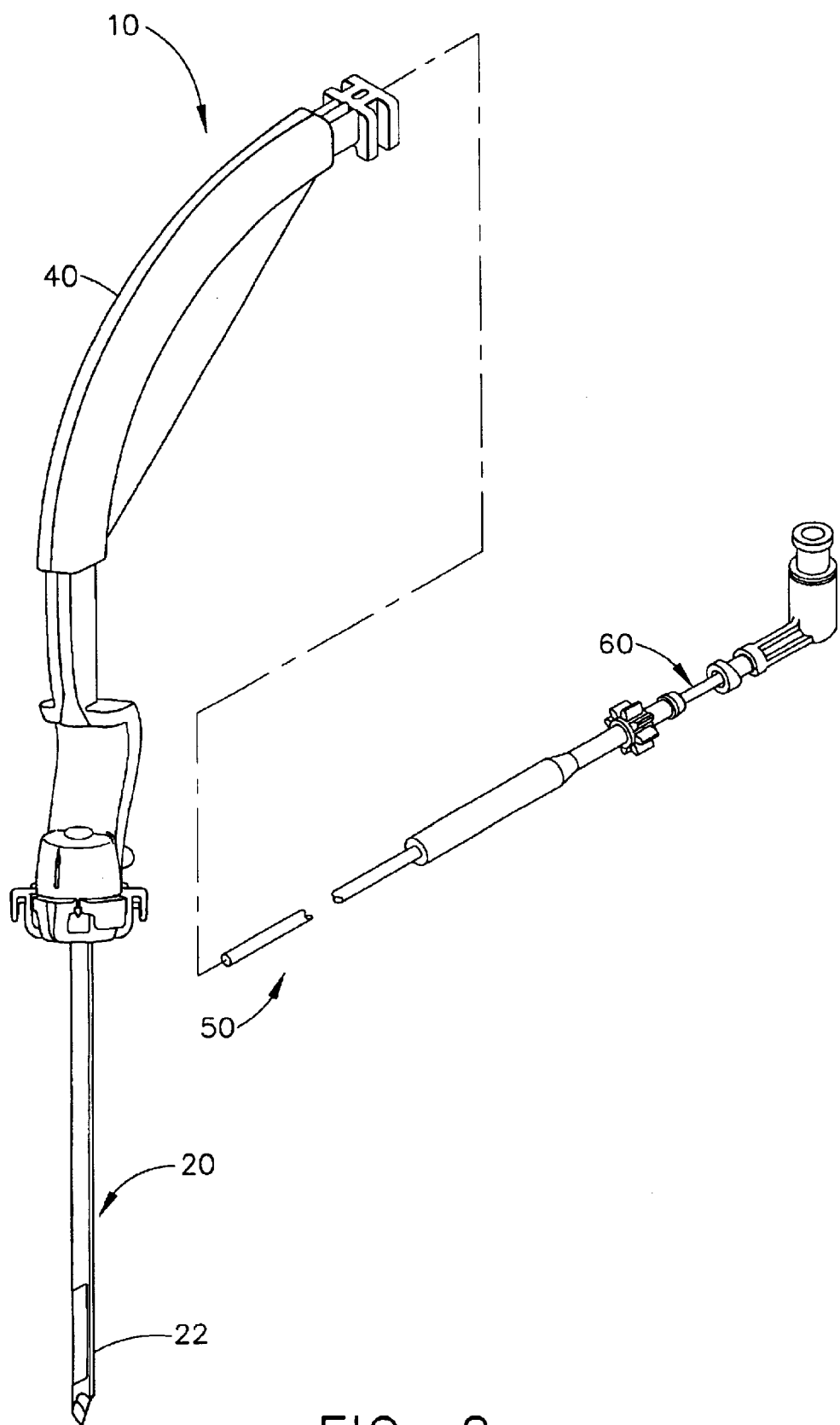
FIG. 2 is an isometric view of a biopsy probe of the present invention.

Attention is now drawn to FIG. 2 which is an isometric view of the preferred embodiment of probe 10. Probe 10 is a coaxial assembly of three elongated elements: a piercer 20, a cutter 50, and a tissue remover 60. Tissue remover 60 moves slideably within cutter 50 which, in turn, moves slideably within frame 40 and piercer 20. Cutter 50 and tissue remover 60 contain flexible elements, as will be described later. Probe 10 generally is used as follows: The skin of a surgical patient is disinfected. A local anesthetic such as lidocaine hydrochloride is injected by hypodermic needle into the tissue. A small incision is made in the skin of the surgical patient. Then piercer 20 is placed into that incision and pierced into the tissue of the surgical patient. Piercer 20 is advanced to the tissue area of interest by the movement of three axis positioning head 98. During this step cutter 50 is completely advanced in its distal direction. Once the tissue of interest is accessed by piercer 20, cutter 50 is partially retracted in the proximal direction and the tissue to be extracted is drawn by vacuum into port 26 on distal end 22 of probe 10. Cutter 50 is then actuated by the cutter motor of driver 100 and manually advanced distally using cutter advance knob 113. This severs the tissue sample captured in distal end 22 of probe 10. Afterwards, cutter 50 is manually retracted in the proximal direction, transporting the tissue sample to outside the patient's body. Tissue remover 60 then releases or "knocks-out" the tissue sample from cutter 50, so that the tissue sample may be retrieved for analysis.

Figure 3:
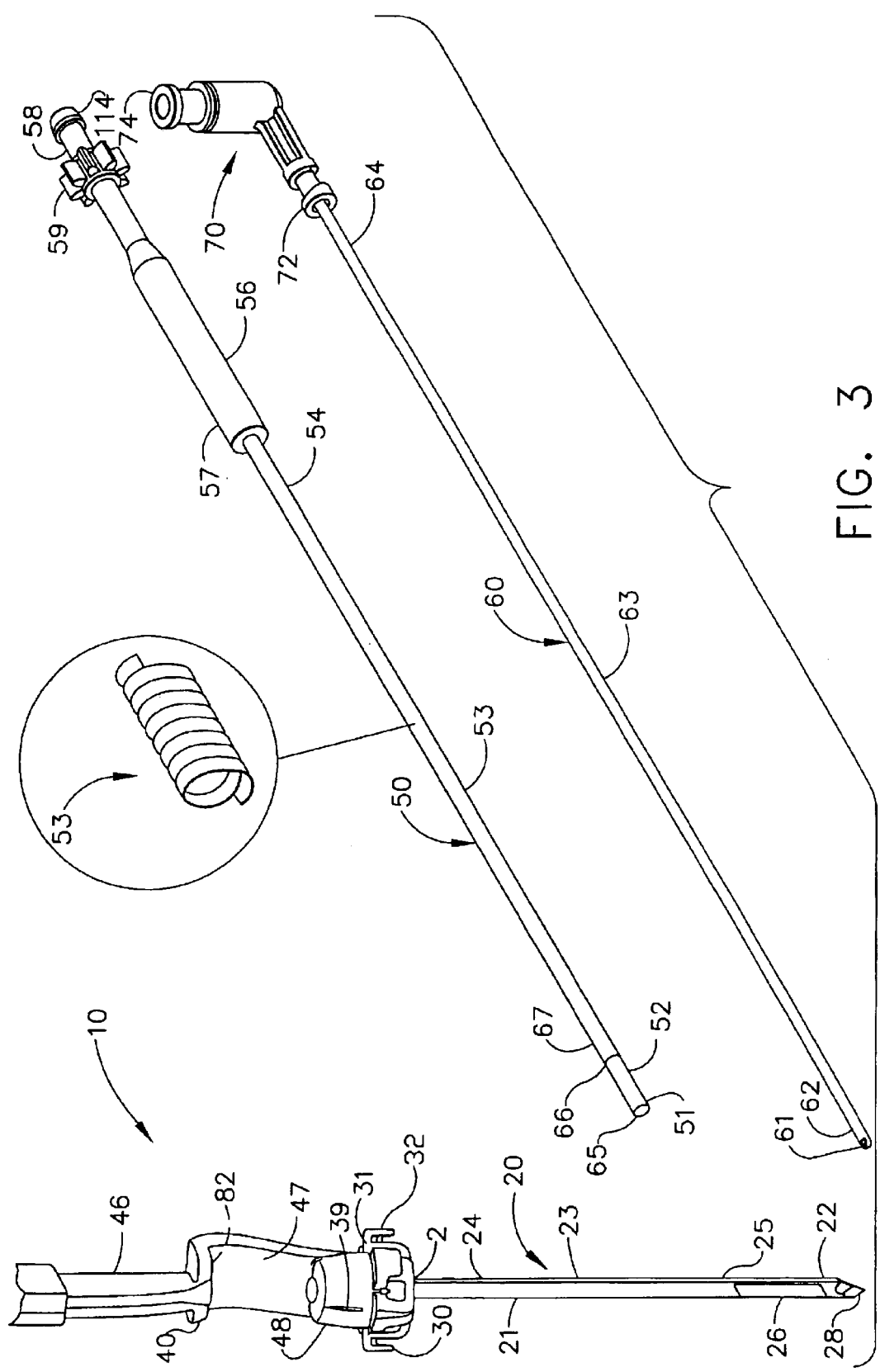
FIG. 3 is an exploded isometric view of the biopsy probe of FIG. 2.
Figure 4:
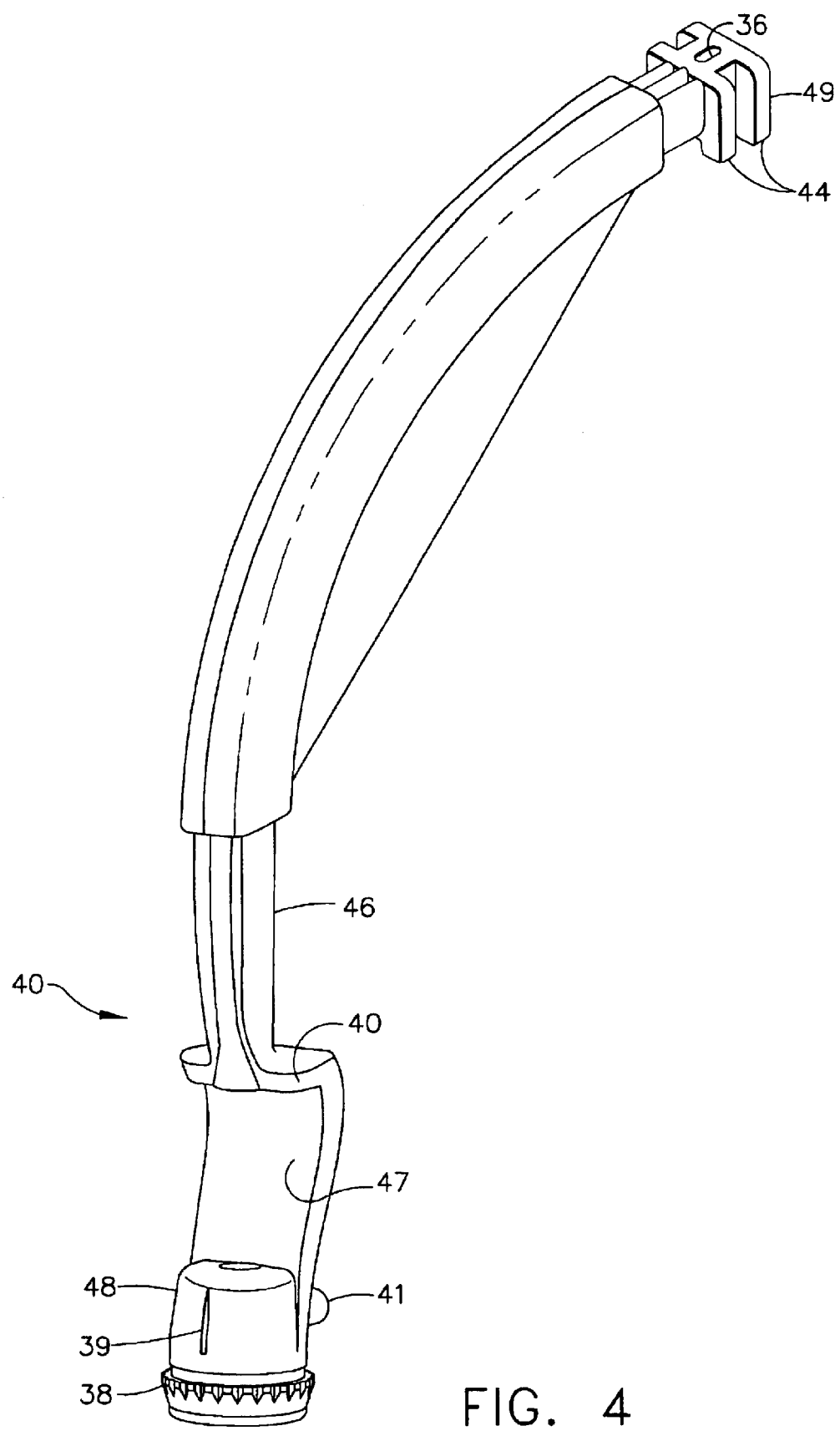
FIG. 4 is an isometric view of a probe frame of the biopsy probe of FIG. 2.

Referring to FIGS. 2 through 4, piercer 20 includes a frame 40 which may be made from a rigid, medical grade plastic. Frame 40 is generally arcuate in shape, forming an arc of approximately ninety degrees in the preferred embodiment, and may be more or less as may be dictated by the mounting needs for the x-ray imaging machine. Frame 40 has a distal end 48 and a proximal end 49. Frame hole 45 (See FIG. 5) extends longitudinally through frame bushing 46 communicating between the distal end 48 and proximal end 49 of frame 40. A pair of mounting fins 44 are located on proximal end 49 of frame 40. Mounting fins 44 are removably inserted into a mounting fork 102 of driver 100 as depicted in FIG. 1, thus anchoring probe 10 to driver 100.

Teeth 38, which comprise a plurality of raised ribs, and marker 39, a single raised rib, are located at the distal end 48 of frame 40 and interface with positioning wheel 30, which will be described in more detail later. Tissue sampling surface 47 at the distal end 48 of frame 40 is where a tissue sample extracted from within the surgical patient is removed from probe 10.

Tubular piercing element 25 is well known in the art and has a proximal end 24 and a distal end 22 and is rotatably attached to the proximal end 48 of frame 40 by a hub 2 (See FIG. 5) and a positioning wheel 30. Piercing element 25 is preferably made from plastic or stainless steel and includes an upper lumen 21 and a lower lumen 23. Rectangular port 26 on distal end 22 of piercing element 25 is located on upper lumen 21 and is provided for receiving the tissue that is to be extracted from the surgical patient. Rotation of positioning wheel 30 by the surgeon allows positioning of rectangular port 26 in distal end 22 of piercer 20. A positional indicator 31 on wheel 30 may be referenced to a marker 39 on frame 40 of probe 10. By changing the position of port 26, the surgeon may access tissue from anywhere around distal end 22 of piercer 20. Piercing tip 28 is attached to distal end 22 of piercing element 25 and pierces into the tissue of the surgical patient. Piercer 20 further comprises a lower lumen 23 which has a plurality of small holes (not shown) in distal end 22 for the communication of port 26 to first reservoir 90. In the present embodiment, this first reservoir is a vacuum source so that the prolapse of tissue into port 26 is greatly enhanced.

A plurality of teeth 38 are located around the periphery of distal end 48 of frame 40. Teeth 38 are for interaction with flutes 32 (not shown) of positioning wheel 30 (see FIG. 1) so that a tactile feedback is provided to the user while adjusting the location of port 26 on distal end 22 of piercer 20. In addition to the tactile feedback, teeth 38 are a holding means for the orientation of port 26, and also a referencing means. That is, the surgeon may count the number of "detents" felt when rotating positioning wheel 30, while looking at the relationship between positional indicator 31 on wheel 30 and marker 39 on frame 40, in order to understand the radial orientation of port 26 on distal end 22 of piercer 20.

Now referring again to FIGS. 1 and 3, cutter 50 comprises a distal end 52, a proximal end 58, and a flexible member extending therebetween. Cutter 50 further comprises a cutter shank 56 having a distal end 57 fixedly attached to a proximal end 54 of a hollow flexible cutter tube 53. Flexible cutter tube 53 can be made of PVC or any other flexible thermoplastic polymer or a superelastic alloy such as nitinol. In an alternate embodiment flexible cutter tube 53 is made of a tubular shape constructed of wound stainless steel wire, similar to a compression spring, as shown in the enlarged, encircled portion of FIG. 3. A longitudinal passage through cutter shank 56 (not visible) communicates with a longitudinal passage through flexible cutter tube 53. On the distal end of cutter 50 is a cutter blade 51. Cutter blade 51 has a distal end 65 and proximal end 66. Cutter blade 51 is preferably made by the sharpening of the circumference of distal end 65 of cutter blade 51, which is preferably made of a stainless steel. Proximal end 66 of cutter blade 51 is fixedly attached to distal end 67 of flexible cutter tube 53. A longitudinal passage through cutter blade 51 communicates with a longitudinal passage through flexible cutter tube 53. On proximal end 58 of cutter 50 is a cutter gear 59, which is preferably integrally molded with cutter shank 56. A proximal cutter seal 114 is attached to the most proximal end of cutter 50.

Cutter gear 59 is for operational engagement with an elongated gear 106 of driver 100. When probe 10 is inserted into driver 100, cutter gear 59 is positioned into cutter advance fork 112 of the driver. Cutter advance fork 112 is attached to cutter advance knob 113 so that movement of knob 113 causes the like movement of cutter 50. Cutter 50 reciprocates axially within upper lumen 21 of piercer 20 as the surgeon manually operates advancing knob 113. As cutter 50 is moved distal and proximal by operation of cutter advance knob 113, cutter gear 59 moves along elongated gear 106 of driver 100, while maintaining operational engagement. The electric motor (not shown) of the driver rotates cutter 50 at a high rate of speed.

As best illustrated in FIG. 3, tissue remover 60 comprises a remover tube 63, which has a proximal end 64, a distal end 62, and a longitudinal axis extending therebetween. Tissue remover 60 slides freely through proximal cutter seal 114. On proximal end 64 of remover tube 63 is attached a valve 70 having a distal end 72, a proximal end 74 which contains a Luer connector, and a passageway therethrough. Valve 70 provides for the flow of air and fluids from tissue remover 60 to second reservoir 94 via second tube 95 and a connector 97 (see FIG. 1). Remover tube 63 is hollow and in the present embodiment made of flexible PVC or other flexible thermoplastic resin. In an alternate embodiment, since remover tube 63 is held fixed with reference to probe frame 40, remover tube 63 is made of a rigid material such as stainless steel and pre-formed in an arcuate shape to match the arc of probe frame 40. A distal tip 61 (also referred to simply as a structure) on distal end 62 of remover tube 63 is configured so as to allow the passage of air and fluids and to block the passage of tissue particles larger than what may pass through tissue remover 60 and valve 70. Distal tip 61 prevents the loss of tissue into the reservoir, which may otherwise be collected for pathological analysis. The length of remover tube 63 is such that when cutter 50 is retracted to the first position, distal tip 61 of remover tube 63 is approximately adjacent to cutter blade distal end 65 of cutter blade 51. This arrangement allows the tissue sample retrieved in distal end 52 of cutter 50 to be forced out of the same by distal tip 61 of tissue remover 60 when cutter 50 is retracted to the first position. The tissue sample may then drop onto tissue sample surface 47 of probe 10.

Figure 5:
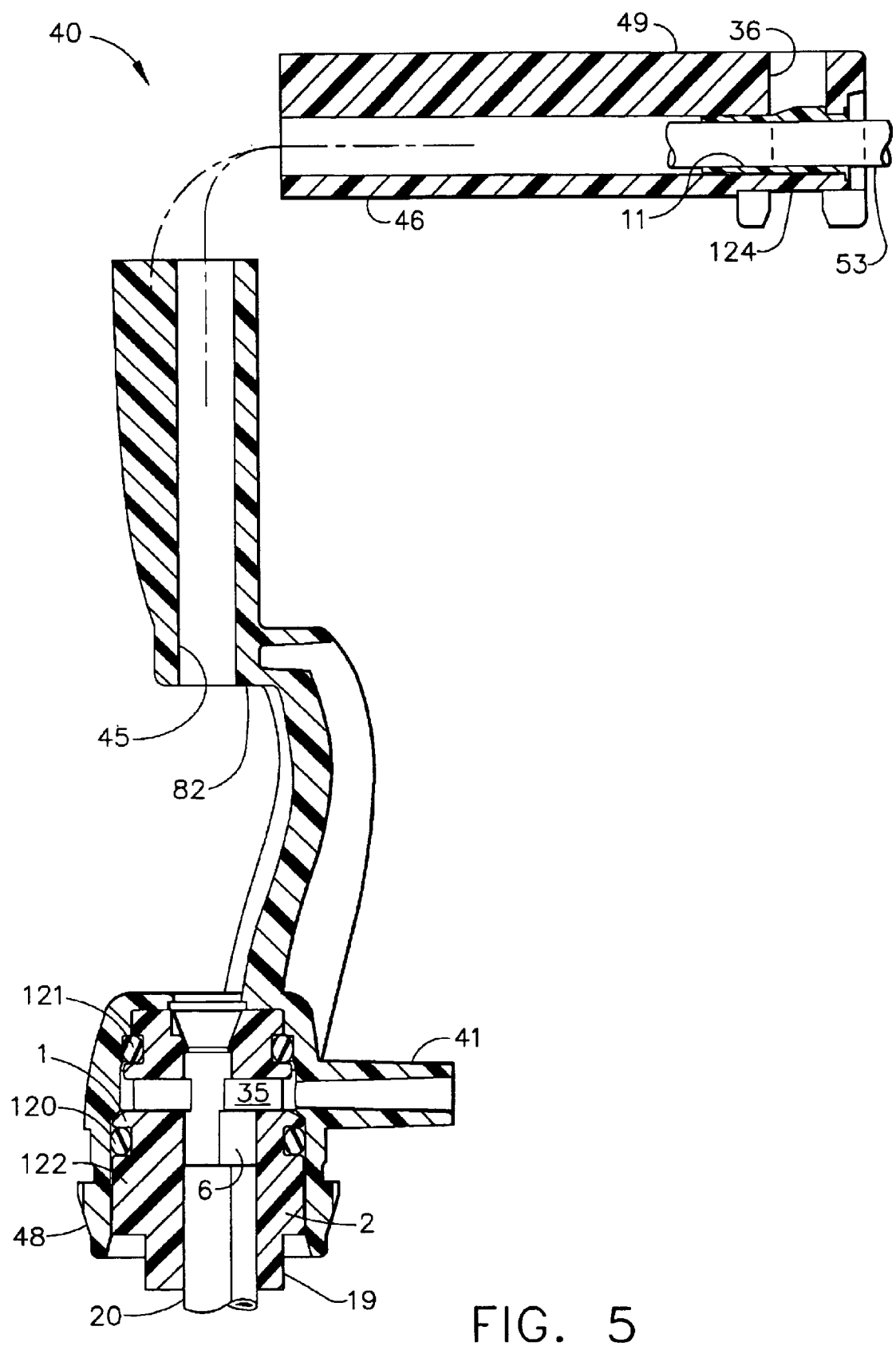
FIG. 5 is a longitudinal sectional view of the probe frame of FIG. 4 illustrating the internal structures assembled into its distal and proximal ends.

Referring now to FIG. 5, flexible cutter tube 53 fits closely yet slides freely in frame hole 45 which extends longitudinally through frame bushing 46 of piercer 20. When cutter 50 is retracted to its most proximal position, cutter blade 51 of cutter 50 is approximately adjacent to frame surface 82 of piercer 20 so as to allow free access to sampling surface 47 (See FIG. 4) for retrieval of the tissue sample.

Distal frame seal 1 is shown assembled into distal end 48 of frame 40 and rotatably supports proximal end 24 of piercing element 25. Distal frame seal 1 comprises hub 2 and a first O-ring 120 and a second O-ring 121. Hub 2 further comprises a hub step 19, wherein hub step 19 is a supporting means for positioning wheel 30 (see FIG. 3). A first radial space 122, which is occupied by part of distal frame seal 1, is defined by the radial clearance between piercer 20

(partially shown) and proximal end 48 of frame 40. A lower lumen vacuum boss 41 is in alignment between two O-rings 120 and 121 so as to allow vacuum to be delivered through passages 35 and into opening 6 of distal frame seal 1. First tube 91 (see FIG. 1) from first reservoir 90 is a flexible, medical grade tube which may fit tightly over vacuum boss 41. Proximal end 24 of lower lumen 23 of piercing element 25 is inserted into opening 6 of distal frame seal 1 so that the vacuum may be delivered through lower lumen 23 and to port 26 on distal end 22 of piercer 20.

Proximal frame seal 11 is shown assembled into proximal end 49 of frame 40 and is held in position by a protrusion projecting into hole 36 in frame 40. The proximal frame seal occupies a second radial space 124 defined by the clearance between flexible cutter tube 53 and proximal end 49 of frame 40. Proximal frame seal 11 substantially prevents the flow of fluids through the second radial space.

It should be noted that second reservoir 94 is a vacuum source which facilitates the removal of the fluids from within probe 10, and which facilitates the transport of the tissue sample from port 26 to tissue sampling surface 47 (see FIG. 1). Because tissue remover 60 is inserted within cutter 50 which is inserted in upper lumen 21 of piercer 20, the vacuum source is connected to upper lumen 21 as well and assists in drawing tissue into port 26 prior to cutting of the tissue by cutter blade 51. In addition to the removal of fluids from probe 10, the vacuum provides a means of releasably attaching the tissue sample to the end of tissue remover 60 so that once severed, the sample may be held in distal end 52 of flexible cutter tube 53 and transported from port 26 of piercer 20 to outside the patient's body to tissue sampling surface 47 of probe 10.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A medical device for obtaining a tissue sample, the device comprising:
    an elongated piercing element having a lumen extending at least partially through the elongated piercing element, wherein said elongated piercing element comprises a proximal end, a distal end having a tip for piercing tissue, and a lateral tissue receiving port communicating with the lumen;
    an elongated cutter having a proximal end, a distal end for cutting tissue, and a body connecting the distal and proximal ends, wherein said distal end is disposed coaxially within the said lumen of said piercing element, wherein at least a portion of said body comprises a flexible member, and wherein at least a portion of said flexible member and said proximal end of the cutter are disposed outside of said lumen of said piercing element;
    a cutter driver for providing powered rotation of said cutter; and
    a frame, said frame having a proximal end removably mounted to said cutter driver, said frame having a distal end associated with said proximal end of said elongated piercing element, and said frame having a passageway extending at least partly therethrough for receiving said cutter.

2. The medical device of claim 1 wherein said frame passageway is generally arcuate.

3. The medical device of claim 2 wherein said passageway forms an arc of about ninety degrees between said frame proximal end and said frame distal end.

4. The medical device of claim 1 wherein said body of said cutter comprises a wound construction.

5. The medical device of claim 4 wherein said body of said cutter comprises a wound wire.

6. The medical device of claim 1 wherein said body of said cutter comprises a flexible polymer.

7. The medical device of claim 1 further comprising an elongated tissue remover disposed slidably within said cutter to remove a tissue sample therefrom.

8. The medical device of claim 7 wherein said elongated tissue remover comprises a flexible portion for sliding within a portion of said cutter disposed in said frame passageway.

9. A medical device for obtaining a tissue sample, the device comprising:
    an elongated piercing element having a proximal end, a closed distal end with a piercing tip for piercing tissue, a lumen extending at least partially through the elongated piercing element, and a lateral tissue receiving port spaced proximally of the closed distal end and communicating with the lumen;
    an elongated cutter having a proximal end, a distal end for cutting tissue, and a body connecting the distal and proximal ends, wherein said distal end is disposed coaxially within the lumen of said piercing element, wherein the cutter extends proximally from the lumen of the elongated piercing element, and wherein at least a portion of the cutter extending proximally from the lumen is flexible and capable of taking on a curved shape;
    a cutter driver for providing powered rotation of said cutter; and
    a frame, said frame having a proximal end removably mounted to said cutter driver, said frame having a distal end associated with a proximal end of said elongated piercing element, and said frame having a curved passageway extending at least partly therethrough for receiving said cutter.

10. A medical device for obtaining a tissue sample, the device comprising:
    a generally straight, elongated piercing element having a proximal end, a closed distal end with a piercing tip for piercing tissue, a generally straight lumen, and a lateral tissue receiving port spaced proximally of the closed distal end and communicating with the lumen;
    an elongated cutter having a proximal end, a distal end for cutting tissue, and a body connecting the distal and proximal ends, wherein the distal end of the cutter is positionable with the lumen of the piercing element, wherein the cutter extends proximally from the lumen of the piercing element, and wherein at least a portion of the cutter extending proximally from the lumen of the piercing element is flexible and capable of taking on a curved shape; and
    a member disposed proximally of the proximal end of the elongated piercing element, the member having a curved passageway therein for receiving a flexible portion of the cutter.

* * * * *